United States Patent [19]

Ennis, III

[11] Patent Number: 4,693,706
[45] Date of Patent: Sep. 15, 1987

[54] TWO COMPARTMENT MIXING SYRINGE

[75] Inventor: James F. Ennis, III, Preston, Conn.

[73] Assignee: Mark L. Anderson, Elmwood, Wis.

[21] Appl. No.: 895,237

[22] Filed: Aug. 11, 1986

[51] Int. Cl.$^4$ .............................................. A61M 5/00
[52] U.S. Cl. ....................................... 604/87; 604/220
[58] Field of Search ....................... 604/56, 82, 87-90, 604/191, 218, 220, 222

[56] References Cited

U.S. PATENT DOCUMENTS

| | | | |
|---|---|---|---|
| 2,619,087 | 11/1952 | Oclassen et al. | 604/220 |
| 2,724,385 | 11/1955 | Lockhart | 604/220 |
| 3,255,752 | 6/1966 | Dick | 604/89 |
| 3,340,873 | 9/1967 | Solowey | 604/87 |
| 3,354,882 | 11/1967 | Coanda | 604/222 |
| 3,739,947 | 6/1973 | Baumann et al. | 604/87 X |
| 4,171,698 | 10/1979 | Genese | 604/88 |
| 4,412,836 | 11/1983 | Brignola | 604/87 |

Primary Examiner—Dalton L. Truluck
Attorney, Agent, or Firm—Edward H. Loveman

[57] ABSTRACT

A mixing syringe having an inner cylindrical barrel open at one end, and closed at its other end by a thin, tough, membrane bonded thereto. The barrel may contain a first liquid. A plunger inserted in the barrel has a sliding, sealing head which applies pressure to the liquid to rupture the membrane when the plunger is advanced. The barrel is slidably inserted in an open end of an outer barrel in sealing relationship therewith, and has a tip on the other end of the outer barrel. The outer barrel contains a liquid or other material to mix with the first liquid when the membrane is ruptured. The mixture is discharged from the outer barrel via the tip when the inner barrel is advanced axially in the outer barrel.

13 Claims, 8 Drawing Figures

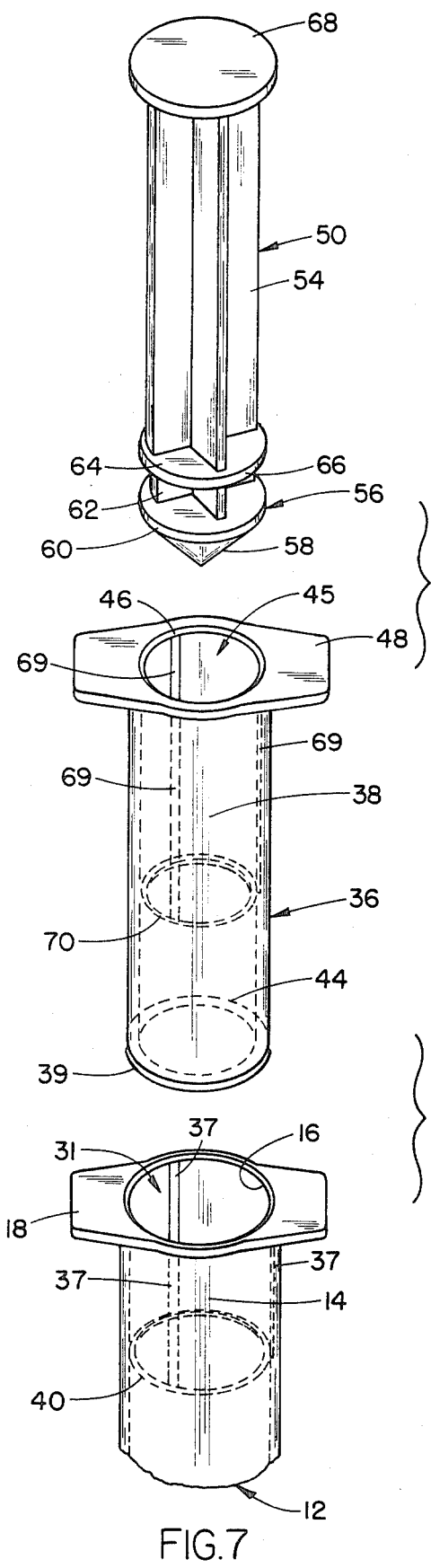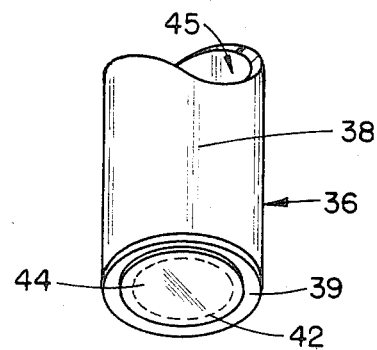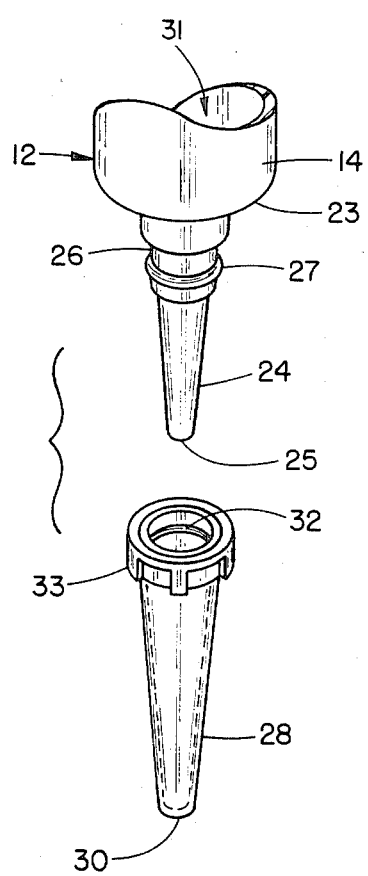
FIG.6
FIG.8
FIG.7

TWO COMPARTMENT MIXING SYRINGE

FIELD OF THE INVENTION

This invention relates to the art of two compartment mixing syringes, and more particularly concerns a mixing syringe having an inner barrel provided with a frangible sealing diaphragm.

BACKGROUND OF THE INVENTION

Mixing syringes having two compartments or chambers are known in the prior art. These syringes generally consist of an outer barrel with a nipple or cannula at one end, and having an open other end. An inner barrel having a dispensing end is inserted through the open end of the outer barrel and extends partially into the outer barrel. A plunger is inserted into the open other end of the inner barrel. A seal is provided at the dispensing end of the inner barrel. The seal in these prior syringes are adapted to be displaced by pressure exerted on a fluid in the inner barrel when the plunger is moved axially in the inner barrel. The seal yields to the fluid pressure and the fluid in the inner barrel flows into the outer barrel to mix with liquid, powder or solids contained in the outer barrel. After mixing is completed the inner barrel may be axially advanced in the outer barrel to cause the mixture to flow into the cannula and out of the syringe. Typical mixing syringes of the type aforedescribed are shown in U.S. Pat. Nos. 3,052,239; 3,380,451; 3,685,514; and 4,464,174.

DESCRIPTION OF THE PRIOR ART

The prior mixing syringes have several disadvantages. A principal difficulty is the fact that they are not wholly reliable. Their biased or sliding seals may be inadvertently or accidentally displaced with a small amount of pressure, so that fluid undesirably leaks from the compartment in the inner barrel to the compartment in the outer barrel.

Another objection is the relatively high cost of manufacture of the seals. For example, the syringe of U.S. Pat. No. 4,464,174 requires special molds to make the movable plugs used as sealing members, which molds are very expensive to manufacture. Other mixing syringes have very critical dimensions requiring expensive machinery to insure precision. Still other syringes require hand assembly of the seals and barrels which involves costly hand labor.

SUMMARY OF THE INVENTION

In accordance with the invention, a mixing syringe has an outer cylindrical barrel with an open end provided with radially extending finger grips. At the other end of the barrel is an open tip. Inserted in the open end of the outer barrel is a cylindrical inner barrel having a dispensing end closed by a membrane. The other end of the inner barrel is open and provided with radially extending finger grips. Inserted in the open end of the inner barrel is a plunger which is force fitted so that it requires pressure to advance it in the inner barrel. When the plunger is advanced axially in the inner barrel with sufficient force, the pressure on the fluid in the inner barrel will rupture the sealing membrane by bursting or breaking the bond between the membrane and the dispensing end of the inner barrel, causing the fluid to discharge into the outer barrel to mix with the liquid or solid contents contained therein.

OBJECTS OF THE INVENTION

It is therefore, a principal object of the prsent invention is to provide a mixing syringe which overcomes the above and other difficulties and disadvantages of prior mixing syringes.

Another object of the present invention is to provide a two compartment mixing syringe with an improved seal which is inexpensive to manufacture and assemble on the dispensing end of the inner barrel of the syringe.

A further object of the present invention is to provide a mixing syringe with such a seal that inadvertent pressure on the plunger will not be sufficient to displace the seal and cause undesired mixing of the fluid in the inner barrel with the material in the outer barrel.

Still another object of the present invention is to provide a mixing syringe with a seal which is not biased closed, but is instead hermetically and permanently sealed by a fixed, frangible membrane bonded to the dispensing end of the inner barrel of the syringe; the membrane being separable or rupturable by pressure exerted by a plunger moving in the inner barrel.

Yet another obect of the present invention is to provide a two compartment mixing syringe which after discharge cannot be refilled and reused.

These and other objects and many of the attendant advantages of this invention will be readily appreciated as the same becomes better understood by reference to the following detailed description when considered in connection with the accompanying drawings.

DESCRIPTION OF THE DRAWINGS

FIG. 6 is an enlarged, exploded perspective view of a portion of the inner barrel showing the membrane sealed end;

FIG. 7 is an exploded perspective view of the plunger, inner barrel and a portion of the outer barrel; and FIG. 8 is an enlarged view of the outer barrel tip and cap.

DESCRIPTION OF THE PREFERRED EMBODIMENT

Figure 1:
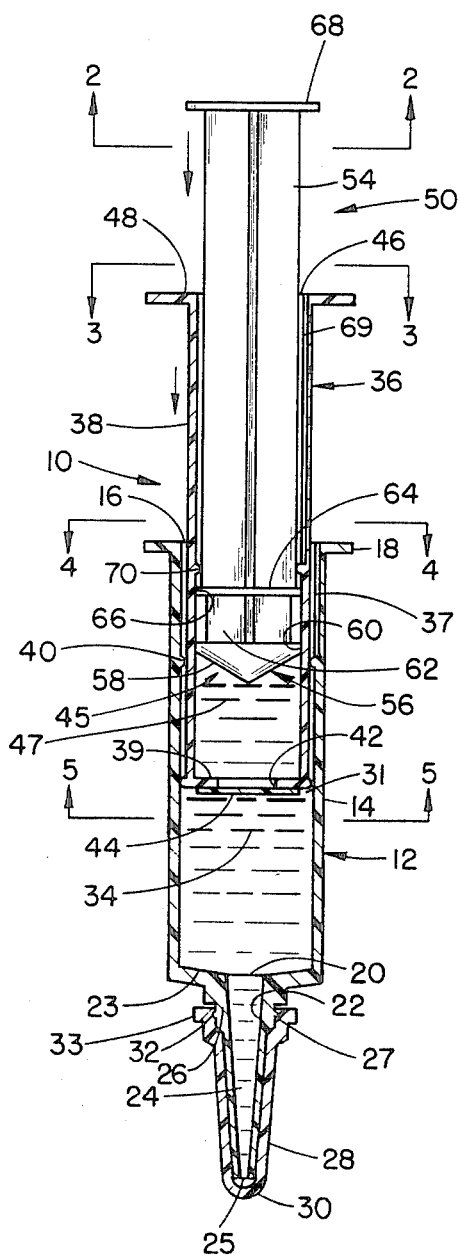
FIG. 1 is an axial sectional view of a mixing syringe embodying the invention.
Figure 2:
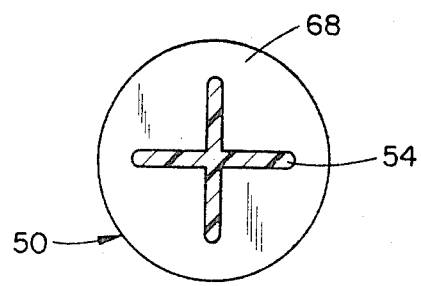
FIGS. 2, 3, 4, and 5 are enlarged cross sectional views taken along lines 2—2, 3—3, 4—4, and 5—5 respectively of FIG. 1.
Figure 3:
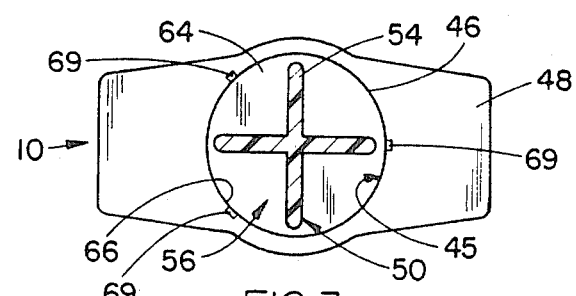
Figure 4:
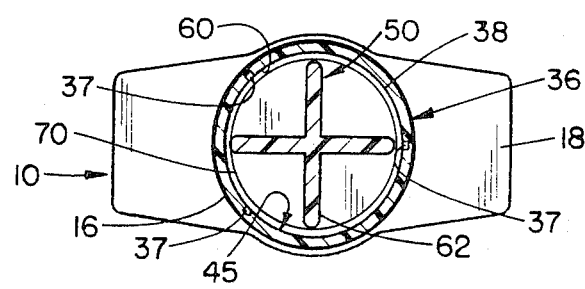
Figure 5:
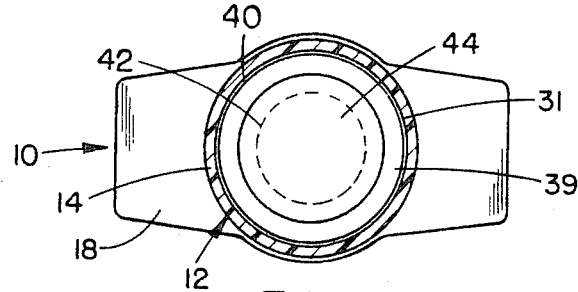

Referring now to FIGS. 1–8 of the drawings wherein like reference characters designate like or corresponding parts throughout, there is shown a mixing syringe generally designated by reference numeral 10 having an outer hollow barrel 12. The barrel 12 has a thin cylindrical wall 14 open at one end 16 and provided with a radially extending finger grip 18 thereat. A bead or detent 40, which is 0.010" smaller than the inside diameter of the outer barrel 12, is provided inside the barrel 12, the purpose of which will be hereinafter more fully explained. The other end of the barrel 12 has a narrow opening 20 communicating with a passage 22 in a conical tip or cannula 24 having an open end 25. The tip 24 is integral with an annular end wall 23 of the barrel 12 and is provided with a cylindrical boss 26 near the end wall 23. On the boss 26 is a circumferential bead or detent 27 (see FIG. 8). Removably mounted on the tip or cannula 24 is a conical cap 28 closed at its apical end 30. The cap 28 is formed with an inner circumferential bead 32 which engages on the boss 26 just above the bead 27. On the wide end of the cap 28 is a circumferential finger grip 33. The cap 28 forms a hermetic seal, but it may be snapped off from the cannula 24 to clear the opening 25 for discharging a fluid mixture from the barrel 12. Inside the barrel 12 and defining a compartment 31 may be a quantity of liquid 34 or other material in powdered, viscous or solid form.

Axially aligned with the barrel 12 and inserted in the open end 16 is a tubular inner barrel 36 having a cylindrical bead 70, which makes a snug, sealing, and friction fit with the wall 14 of the barrel 12. Also formed on the inside of the barrel wall 14 are three angularly spaced elongated grooves 37 which may be each 0.125" wide and 0.010" deep. The grooves 37 begin at the open end 16 and terminate at the bead 40 to permit venting of the compartment 31 when the barrel 36 is advanced therein. The inner end of the barrel 36 has an annular end wall 39 with a central opening 42 closed by a thin, membrane 44 which may be frangible and bonded at its rim to the wall 39 around the opening 42. The membrane 44 may be a very strong, and tough film made of polyethylene, mylar, or equivalent material, which may burst, rupture, fracture or separate, when sufficient pressure is exerted upon it, but which cannot be inadvertently or accidentally broken by any force normally encountered in storage, shipment, or handling of the syringe. Inside the inner barrel 36 is a circumferential bead or detent 70 which is 0.010" smaller then the inside diameter of the inner barrel and acts as a stop for a plunger 50 as will be hereinafter more fully described. Inside a compartment 45 formed in the barrel 36, between the cylindrical walls 38 and the membrane 44 and the end wall 39 is a quantity of liquid 47 to be mixed with the liquid or other material 34 in the compartment 31. At the other open end 46 of the barrel 36 is a radially extending finger grip 48. Formed within the barrel wall 38 are three angularly spaced elongated grooves 69 which may be 0.125" wide and 0.010" deep and extend from the open end 46 to the bead 70 to permit venting of the compartment 45.

Force fitted inside the barrel 36 and slidable therein when sufficient force is exerted is an elongated plunger 50 which has a shaft defined by crossed, flat, longitudinal stiffening ribs 54. At the inner end of the plunger 50 is a sealing head 56 which has a solid conical tip 58 formed with a cylindrical outer edge 60 disposed in sliding but sealing engagement with the inner side of the barrel wall 38. Four short narrow crossed ribs 62 integrally connect the tip 58 to a narrow circular end wall 64 whose cylindrical outer edge 66 is disposed in sliding but sealing engagement with the inner side of the barrel wall 38. At the outer end of the plunger 50 is a circular head 68 which serves as a finger grip or hand grip for advancing the plunger 50 axially inside the barrel 38.

It should be noted, when a desired amount of liquid 47 is inserted in the barrel 36, the volume must be such that when the plunger 50 is inserted into the barrel 36, the sealing head 56, of the plunger 50, is below the bead or detent 70 to prevent any leakage of liquid through the grooves 69. Similarly, when a desired amount of liquid, powder, paste or other material 34, is placed into the barrel 12 the volume must be such that when the barrel 36 is inserted therein the end wall 39 extends below the bead or detent 40 to prevent leakage of the material 34 through the grooves 37.

In operation, the barrel 12 is filled with the material 34 as described above and the barrel 36 (with the liquid 47 therein) is inserted axially into the compartment 31 until the end wall 39 of the barrel 36 contacts the surface of the material 34. The air in the compartment 31 is vented out of the barrel 12 via the grooves 37, until the end wall 39 is below the bead or detent 40. Then the plunger 50 may be inserted through the open end 46 of the barrel 36 until the head 56 contacts the surface of the liquid 47. The air above the liquid 47 is vented out of the barrel 36 via the grooves 69 until the wall 60 of the plunger 50 is below the bead 70. The wall 14 of the barrel 12 is preferably made of a flexible plastic material such as polyethylene having a thickness of about 0.040 inches so that the wall 14 will flex circumferentially so that the bead 40 will grip the inner barrel 36 in a liquid-tight seal. The head 56 of the plunger 50 may have a diameter at the walls 60 and 66 which is slightly larger than the inside diameter of the wall 38 (0.0006" to 0.010") to insure that the head is gripped in a slidable, liquid-tight seal, while the wall 38 flexes circumferentially. The membrane 44 may be made of a thin plastic material, such as polyethylene having a thickness of about 0.0015 inches, which material is sufficiently tough to insure that the membrane will not rupture when subjected to accidental, inadvertently applied forces, but will rupture when sufficient force is applied by axial advancement of the plunger 50 in the barrel 36. The wall 38 of the barrel 36 has a thickness of about 0.040" to insure that the membrane 44 will rupture or separate from the wall 39 before the barrel 36 will break when the plunger 50 is exerting maximum rupturing force upon the membrane 44.

The mixing syringe 10 may be held by the finger grip 48 with the thumb exerting pressure on the plunger head 68 to apply sufficient pressure on the membrane 44 so that it will rupture or sever its bond with the wall 39. It will be noted that the tip 58 of the head 50 is conical. This configuration provides maximum area for applying pressure to the liquid 47, and is therefore preferred over a head having a flat or blunt end. After the membrane 44 is ruptured, by bursting or severed from the wall 39 the liquid 47 will enter the compartment 31 and will mix with the contents of this comparment as the plunger 50 is advanced into the barrel 36 until the tip 58 abuts the end wall 39 thereby insuring that all the liquid 47 enters the compartment 31. As the liquid 47 enters the compartment 31 the barrel 36 moves up toward the finger grip 18 but the bead 40 acts as a stop to prevent the end wall 39 from moving out of the barrel 12. The mixture of liquid 47 and material 34 will be retained in the barrel 12 due to the cap 28 in which the tip 24 is nested. The cap 28 grips the tip 24 in a liquid-tight sealing relationship since the axial length of the tip 24 is substantially equal to the interior axial length of the cap 28, and the beads 32 and 27 are in mutual engagement. The contents of the compartment 31 may be thoroughly mixed by manually shaking the syringe 10. Thereafter, the cap 28 may be removed and by gripping the finger grip 18 and applying pressure to the plunger 50, both the plunger 50 and the barrel 36 will be axially advanced simultaneously in the barrel 12 to discharge the mixture from the barrel 12 via the tip 24.

It will be noted that the sealing of the barrel 36 at its lower end is effected in a very practical although inexpensive manner. The membrane 44 may be heat sealed, electronically bonded, chemically bond, or sonically bonded to the end wall 39 of the barrel 36, or if desired to the barrel 36. As hereinbeforementioned instead of rupturing the membrane 44 the bond between the membrane 44 and the end wall 39 may be broken by the pressure applied via the plunger 50. The several parts of the syringe 10 may be made by inexpensive mass production plastic working processes. The syringe 10 is economical enough to be discarded after a single usage. If desired a hollow hypodermic type of needle may be attached to the tip 24 for dispensing the mixture from the syringe 10.

It should be understood that the foregoing relates to only a preferred embodiment of the invention which has been by way of example only, and that it is intended to cover all changes and modifications of the example of the invention herein chosen for the purpose of the disclosure which do not constitute departures from the spirit and scope of the invention.

What is claimed is:

1. A mixing syringe, comprising:
   an inner cylindrical barrel open at one end and closed at its other end and defining an inner compartment therein for containing a quantity of a liquid;
   a membrane bonded to the other end of said inner barrel closing the same thereat;
   an outer cylindrical barrel open at one end thereof and defining an outer compartment therein for containing a material to be mixed with said liquid, said inner barrel being axially inserted through said one end of said outer barrel in slidable sealing contact therewith;
   an elongated plunger axially movable in said inner barrel and having a head force fitted in sliding, frictional, sealing contact with said inner barrel for exerting pressure on said liquid when said plunger is advanced axially to rupture said membrane, so that said liquid enters said outer compartment and mixes with said material therein;
   an open tip at the other end of said outer barrel for discharging said mixture of said liquid and said material from said outer compartment, when said plunger and said inner barrel are advanced axially in said outer barrel;
   said inner cylindrical barrel having a stop means intermediate the ends thereof for preventing said elongated plunger from moving axially therefrom when subjected to an inadvertently applied force; and
   said inner barrel having means extending from said stop means to said open end of said inner barrel for venting air therethrough when said elongated plunger is axially moved from said open end to said stop means.

2. A mixing syringe as defined in claim 1, wherein said outer barrel has a stop means intermediate the length thereof, and has venting means extending from said stop means to said open end of said outer barrel to permit venting thereof when said inner barrel is advanced into said outer barrel from said open end to said stop means.

3. A mixing syringe as defined in claim 1, wherein said inner barrel has an annular wall at said other end thereof defining an opening thereat, said membrane being peripherally bonded to said annular wall and closing said opening to keep said liquid isolated from said material to prevent mixing the same together prior to rupture of said membrane.

4. A mixing syringe as defined in claim 3, wherein said membrane is made of a plastic material having such a thickness as to insure rupture thereof when said plunger is axially advanced in said inner barrel, said membrane being tough enough to prevent rupture thereof when subjected to accidentally inadvertently applied forces.

5. A mixing syringe as defined in claim 3, wherein said inner barrel is made of a substance sufficiently thicker and stronger than said membrane to prevent breakage of said inner barrel when said plunger is advanced in said inner compartment to rupture said membrane.

6. A mixing syringe as defined in claim 5, wherein said substance is a flexible material, and wherein said head is slightly larger in diameter than the interior of said inner barrel so that said inner barrel flexes circumferentially at said head to maintain a liquid-tight seal between said head and said inner barrel.

7. A mixing syringe as defined in claim 3, wherein said head of said plunger has a curved tip to provide maximum area for applying pressure to said liquid when said plunger is advanced in said inner compartment.

8. A mixing syringe as defined in claim 7, wherein said head has axially spaced cylindrical walls to maintain said head in liquid-tight sealing contact with said inner barrel.

9. A mixing syringe as defined in claim 3, wherein said tip means is an elongated conical member and an elongated concial cap closed at its apical end and substantially equal in axial length to said member, said member being nested in said cap in sealing engagement therewith to keep said material from falling out of said outer barrel.

10. A mixing syringe as defined in claim 9 further comprising catch means on both said member and said cap for holding the same in quick detachable engagement with said member.

11. A mixing syringe as defined in claim 3, wherein said membrane is made of a first plastic material having such a thickness as to insure rupture thereof when said plunger is axially advanced in said inner compartment, said membrane being tough enough to prevent rupture thereof when subjected to accidental, inadvertently applied forces; and wherein said first barrel is made of a second plastic material having a greater thickness than that of said first plastic material and being sufficiently thick and strong enough to prevent breakage of said inner barrel when said plunger is advanced in said first compartment to rupture said membrane.

12. A mixing syringe as defined in claim 11, wherein said first plastic material is polyethylene having a thickness of approximately 0.0015 inches; and wherein said second plastic material is polyethylene having a thickness of appoximately 0.006 inches.

13. A mixing syringe as defined in claim 11, wherein said second plastic material is sufficiently flexible to grip said head of said plunger frictionally in liquid-tight, sealing sliding relationship to prevent said liquid from seeping past said head and out of said open end of said inner barrel.

* * * * *